United States Patent
Eliachar et al.

(10) Patent No.: US 8,512,358 B2
(45) Date of Patent: Aug. 20, 2013

(54) SUTURING ASSEMBLY

(75) Inventors: Eliahu Eliachar, Haifa (IL); Nir Lilach, Kfar Yehoshua (IL); Gideon Meyer-Brodnitz, Haifa (IL); Ofer Yossepowitch, Petach Tikvah (IL); Dan Sade Hochstadter, Kibbutz Bet Alfa (IL)

(73) Assignee: Keren Medical Ltd., Kibbutz Bet Alfa (IL)

( * ) Notice: Subject to any disclaimer, the term of this patent is extended or adjusted under 35 U.S.C. 154(b) by 103 days.

(21) Appl. No.: 12/523,800

(22) PCT Filed: Jan. 16, 2008

(86) PCT No.: PCT/IL2008/000064
§ 371 (c)(1),
(2), (4) Date: Jul. 20, 2009

(87) PCT Pub. No.: WO2008/087635
PCT Pub. Date: Jul. 24, 2008

(65) Prior Publication Data
US 2010/0082062 A1    Apr. 1, 2010

Related U.S. Application Data

(60) Provisional application No. 60/880,952, filed on Jan. 18, 2007.

(51) Int. Cl.
*A61B 17/04* (2006.01)
(52) U.S. Cl.
USPC ............................ 606/144; 606/148; 606/228

(58) Field of Classification Search
USPC ......... 606/139, 144, 148, 228, 232, 222–225, 606/108; 24/706
See application file for complete search history.

(56) References Cited

U.S. PATENT DOCUMENTS

| | | | | |
|---|---|---|---|---|
| 3,209,422 | A | * | 10/1965 | Dritz ................................ 24/706 |
| 4,669,473 | A | | 6/1987 | Richards et al. |
| 4,705,040 | A | * | 11/1987 | Mueller et al. ................ 606/108 |
| 5,562,683 | A | | 10/1996 | Chan |
| 6,156,044 | A | * | 12/2000 | Kammerer et al. ........... 606/144 |
| 6,319,263 | B1 | * | 11/2001 | Levinson ....................... 606/144 |
| 6,514,271 | B2 | | 2/2003 | Evans et al. |
| 7,128,753 | B1 | * | 10/2006 | Bonutti et al. ................ 606/232 |

OTHER PUBLICATIONS

International Preliminary Report on Patentability published Jan. 12, 2010 for PCT/IL2008/000064 filed Jan. 16, 2008.
International Search Report mailed Sep. 11, 2008 for PCT/IL2008/000064 filed Jan. 16, 2008.
Written Opinion of the International Searching Authority mailed Sep. 11, 2008 for PCT/IL2008/000064 filed Jan. 16, 2008.

\* cited by examiner

*Primary Examiner* — Julian Woo
(74) *Attorney, Agent, or Firm* — The Law Office of Michael E. Kondoudis

(57) ABSTRACT

A suturing needle is disclosed having a main longitudinal axis, a distal sharp portion and proximal portion along said axis. The distal portion is hollowed, and the hollow is approximately parallel to said axis. A further embodiment of the suturing needle is disclosed such that the distal portion comprises a notched open bore located at the needle's extreme distal end. Other embodiments of the suturing assembly are described accommodating a suture in the needle bore.

15 Claims, 6 Drawing Sheets

SUTURING ASSEMBLY

FIELD OF THE INVENTION

The present invention generally relates to a medical device for surgical procedures and specifically to a suturing assembly comprising hollow needle.

BACKGROUND OF THE INVENTION

Surgical procedures these days tend to minimize cut of body tissue by utilizing advanced technology medical devices. Consequently, alternative suturing procedures have to be applied for addressing new substantially further complicated conditions facing the suturing procedures. In the procedure of anastomosis of the urethra and bladder during radical retro-pubic prostatectomy, for example, the attachment of the urethral stump to the bladder neck is particularly difficult and carried out semi-automatically by a surgical medical device. The prior art of suturing manually cannot be applied in these surgical procedures without further body tissue cutting that provides an easier access to the tissue area. The new surgical procedures utilizing for example technologically advanced catheters can be implemented by combining the insertion of catheters into body tubes, tracts or canals and thus restricting the required body tissue cuts. When these surgical procedures are being used, new technologically advanced suturing methods have to be applied for utilizing the advantages of the new surgical procedures to their fullest. Apparently there is a need for suturing devices capable of meeting the challenging conditions imposed by the new surgical procedures.

SUMMARY OF THE INVENTION

It is an object of the present invention to disclose a suturing needle having a hollowed distal portion.

Another object of the present invention is to disclose a suturing needle having a hollowed distal portion, comprising a notched open bore located at said needle's very distal end.

Another object of the present invention is to disclose a suturing assembly comprising said suturing needle with a hollowed distal portion.

Another object of the present invention is to disclose a suturing assembly comprising a needle with a main longitudinal axis having a sharpened tip and hollow distal portion, defining a notched open bore at said needle very distal end.

Another object of the present invention is to disclose the needle as defined in any of the above, wherein said hollow portion of said needle having a bore is adapted to accommodate a suture.

Another object of the present invention is to disclose the suturing assembly as defined in any of the above, wherein said hollow portion of said needle having a bore is adapted to accommodate a suture.

Another object of the present invention is to disclose the needle as defined in any of the above, further comprising a proximal portion, wherein said proximal portion is adapted for coupling with a surgical device.

Another object of the present invention is to disclose the suturing assembly as defined in any of the above, wherein said proximal portion is adapted for coupling with surgical device.

Another object of the present invention is to disclose the suturing assembly as defined in any of the above, further comprising a suture; said suture is extended from said bore.

Another object of the present invention is to disclose the suturing assembly as defined in any of the above, said assembly further comprising a suture, reversibly mounted within said bore.

Another object of the present invention is to disclose the suturing assembly as defined in any of the above, wherein said suture comprising at least one anchoring stopper.

Another object of the present invention is to disclose the suturing assembly as defined in any of the above, wherein said anchoring stopper is spherically shaped.

Another object of the present invention is to disclose a suturing assembly as defined in any of the above, wherein said anchoring stopper is shaped in a shape consisting of a group of various triangles.

Another object of the present invention is to disclose the suturing assembly as defined in any of the above, wherein said anchoring stopper comprising a plurality of rods, umbrella like shaped, having a main axis substantially coinciding with the longitudinal axis of said suture.

Another object of the present invention is to disclose the suturing assembly as defined in any of the above, wherein said hollow portion of the needle is having a bore, adapted to accommodate a suture.

Another object of the present invention is to disclose the suturing assembly as defined in any of the above, said assembly further comprising a proximal portion wherein said proximal portion is adapted for coupling with surgical device.

Another object of the present invention is to disclose the suturing assembly as defined in any of the above, said assembly further comprising a suture; said suture is extended from said bore after inserting said suture into said bore.

Another object of the present invention is to disclose the suturing assembly as defined in any of the above, said assembly further comprising a suture; said suture is extended from said bore via said notch after inserting said suture into said bore.

Another object of the present invention is to disclose the suturing assembly as defined in any of the above, said assembly further comprising at least one anchoring stopper.

Another object of the present invention is to disclose the suturing assembly as defined in any of the above, wherein said suture comprising at least one anchoring stopper.

Another object of the present invention is to disclose the suturing assembly as defined in any of the above, wherein said anchoring stopper is spherically shaped.

Another object of the present invention is to disclose the suturing assembly as defined in any of the above, wherein said anchoring stopper is shaped in a shape consisting of a group of various triangles.

Another object of the present invention is to disclose the suturing assembly as defined in any of the above, wherein said anchoring stopper, comprising a plurality of rods, umbrella like shaped, having a main axis substantially coinciding with the longitudinal axis of said of said suture.

Another object of the present invention is to disclose method of suturing. The method comprising steps selected from a group consisting of obtaining a suturing assembly, comprising (i) a suturing needle with a hollowed distal portion with an open bore at the distal end; and, (ii) a suture reversibly mounted within said bore; suturing a body tissue by piercing said tissue with said distal portion of said needle, until said needle's distal portion extends beyond said pierced tissue; and, retrieving said needle backwards (retrograde) while said suture end, i.e., the end which was inserted into said needle bore, is disengaging from said suturing needle and retained beyond said pierced tissue.

Another object of the present invention is to disclose the suturing method as defined in any of the above, wherein disengaging said retrieved needle from said suture is provided by an anchoring stopper retaining the suture beyond said pierced tissue.

Another object of the present invention is to disclose the method as defined in any of the above, wherein said suturing is provided manually.

Another object of the present invention is to disclose the method as defined in any of the above wherein said suturing is provided automatically by coupling said needle, especially its proximal portion, with a surgical device.

Another object of the present invention is to disclose the method as defined in any of the above, said assembly further wherein said suturing is provided automatically by coupling a plurality of N needles, with a surgical device. N is integer number, being in a non-limiting manner between 2 to 10.

BRIEF DESCRIPTION OF THE FIGURES

The object and the advantages of various embodiments of the invention will become apparent from the following description when read in conjunction with the accompanying drawings wherein.

DETAILED DESCRIPTION OF THE EMBODIMENTS

The following description is provided alongside all chapters of the present invention, so as to enable any person skilled in the art to make use of said invention and sets forth the best modes contemplated by the inventor of carrying out this invention. Various modifications however, will remain apparent to those skilled in the art, since the generic principles of the present invention have been defined specifically to provide a suturing needle having a hollowed distal portion; a suturing assembly comprising a needle with a main longitudinal axis having a sharpened and hollow distal portion, defining a notched open bore at said needle very distal end; and a method of suturing comprising obtaining a suturing assembly, comprising (i) a suturing needle with a hollowed distal portion with an open bore at the distal end; and, (ii) a suture reversibly mounted within said bore; suturing a body tissue by piercing said tissue with said distal portion of said needle, until said needle's distal portion extends beyond said pierced tissue; and, retrieving said needle backwards (retrograde) while said suture end, i.e., the end which was inserted into said needle bore, is retained beyond said tissue.

Figure 1A:
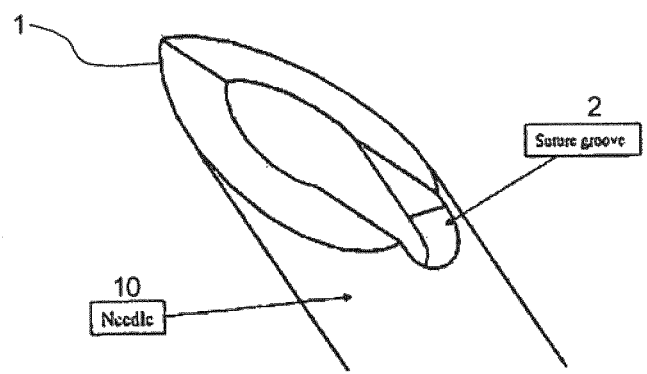
FIG. 1a schematically represents an out-of-scale illustration of the distal portion of the suturing needle according to one embodiment of the present invention.

Reference is now made to FIG. 1a presenting a schematic illustration of the distal portion of the needle. The distal portion of the needle 10 is apt to piercing a body tissue by a sharpened tip 1. The distal portion 10 is hollow and further comprises a bore and least one notch 2 at the very distal end of the bore which are used to accommodate a suture.

Figure 1B:
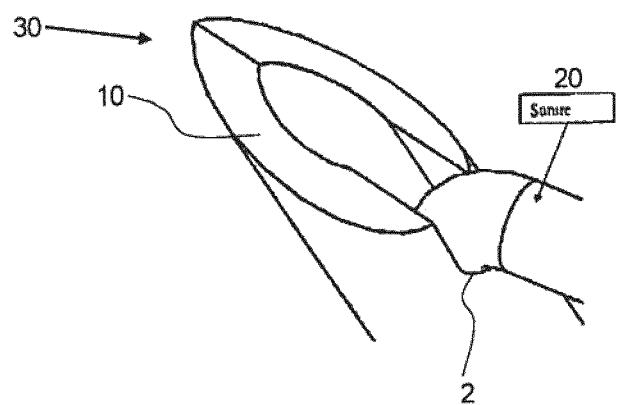
FIG. 1b schematically represents an out-of-scale illustration of the distal portion of the suturing needle with the inserted suture according to another embodiment of the invention.

Reference is now made to FIG. 1b presenting a schematic illustration of a suturing assembly of the distal portion of the suturing needle combined with the suture. The suturing assembly 30 comprises the distal portion of the needle 10 combined with a suture 20 inserted through the notch 2 into the bore. Notch 2 is used for guiding the suture 20 during suture insertion and for retaining the suture inserted to the needle 10 while the suturing assembly 30 is penetrating the body tissue.

Figure 2:
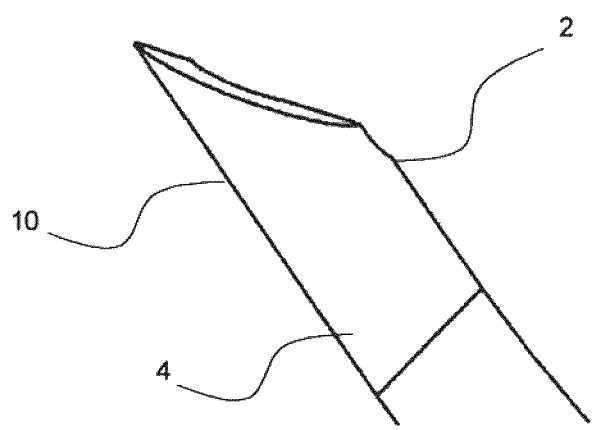
FIG. 2 schematically represents an out-of-scale side view of distal portion of the suturing needle depicting the bore inside the needle according to another embodiment of the invention.

Reference is now made to FIG. 2 presenting a schematic illustration of a side view of the distal portion of the suturing needle. The distal portion of the suturing needle 10 and the sharpened tip 1 are drawn by solid lines, while the concealed notch 2 bore 4, are drawn by dashed lines.

Figure 3:
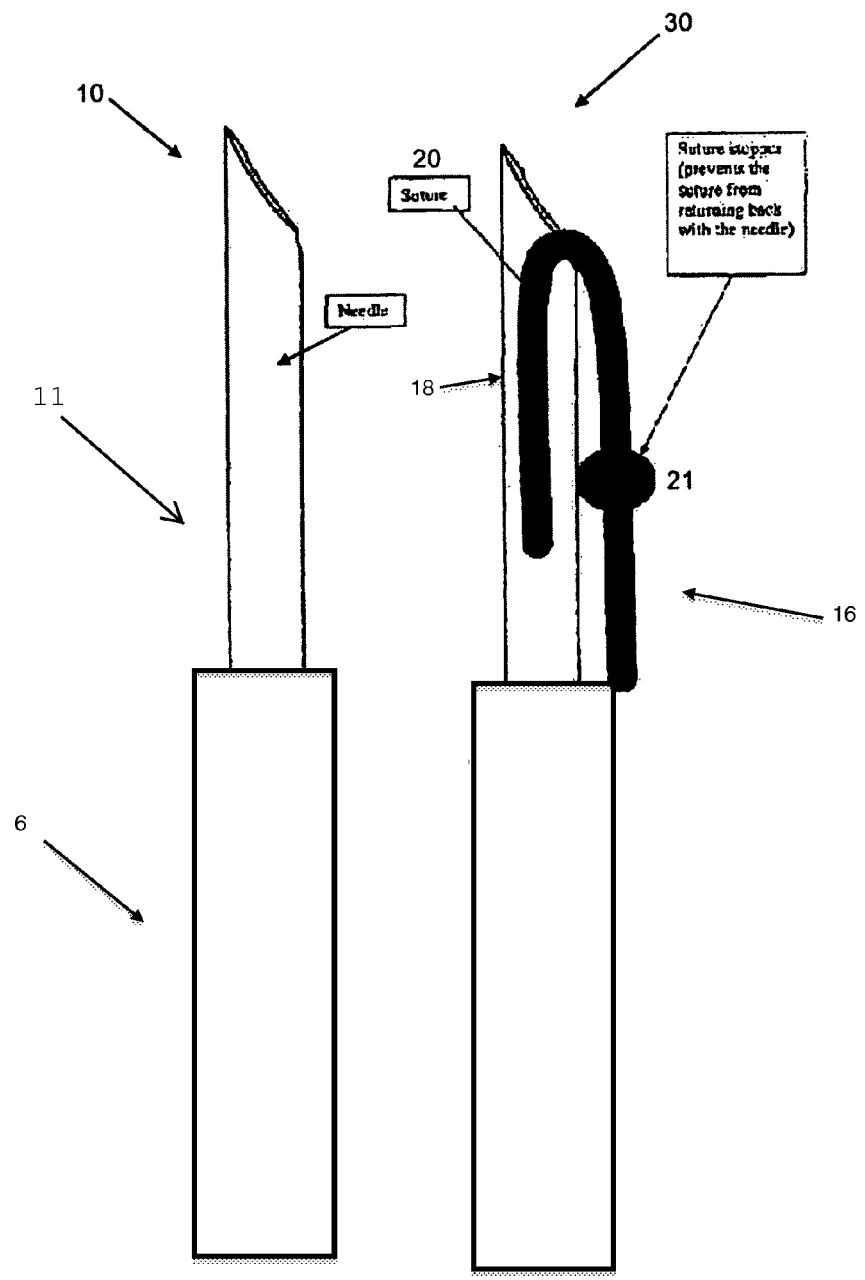
FIG. 3 schematically represents an out-of-scale illustration of the suturing needle combined with an inserted suture according to another embodiment of the invention.

Reference is now made to FIG. 3 presenting a schematic illustration of the distal portion of the needle 10 along with the distal portion of the suturing needle 30. As indicated, the distal portion of the needle is characterized by a main longitudinal axis. The suturing needle includes the suture 20 with a first portion retained in the bore and the notch 2 of the needle. A second portion of the suture 20, adjacent to the first portion extends alone the outer surface of the needle 30. An anchoring stopper 21 is appended to the suture 20 between the first and second portions and used to keep the suture inside the body tissue by blocking the motion of in the proximal direction when the needle is retrieved.

Figure 4:
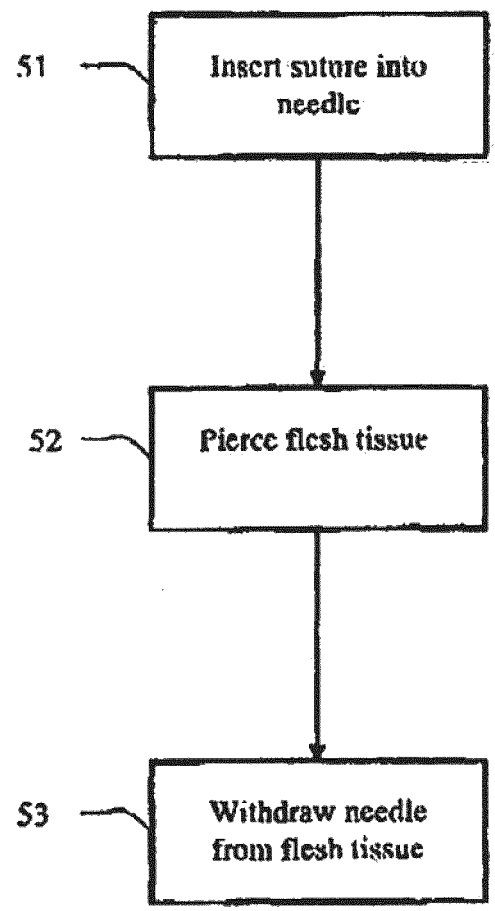
FIG. 4 schematically represents a flow chart of a method according to another embodiment of the invention.

Reference is now made to FIG. 4 presenting a schematic illustration of a flow chart depicting the method of body tissue suturing. In step 51, the surgeon inserts the suture into the bore of the distal portion of the suturing needle for preparing the needle-suture assembly. In the following step 52, the surgeon pierces the tissue for penetrating the suturing needle combined with the suture into the tissue until the suturing needle tip and the anchoring stopper appended to the suture extend beyond the inner wall of the tissue. In the following step 53 the surgeon retrieves the suturing needle so that the needle is traversing in the proximal direction. When retrieved, the suturing needle disengages from the suture since the suture is retained in the tissue by the appended anchoring stopper preventing movement of the suture in the proximal direction. The suture can be tied later by the surgeon to another nearby suture inserted similarly into the body tissue.

Figure 5:
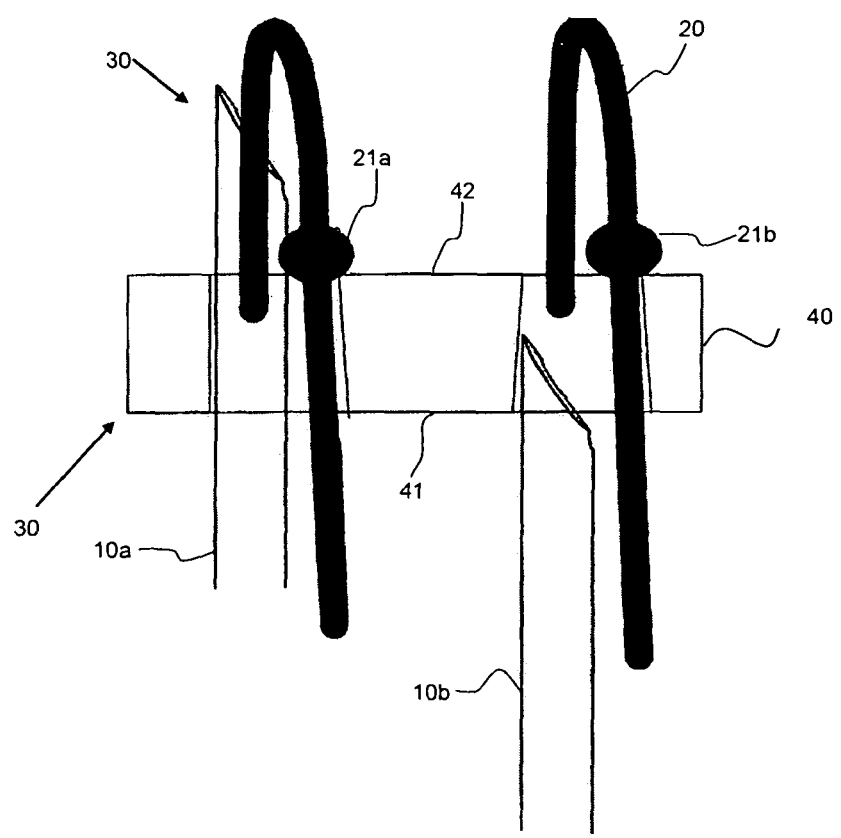
FIG. 5 schematically represents an out-of-scale illustration of the suturing needle with the extended suture at two distinct suturing positions according to another embodiment of the invention; and, FIG. 6 schematically represents out-of-scale illustration of variations of the anchoring according to yet another embodiment of the invention.

Reference is made now to FIG. 5 presenting a schematic illustration showing side by side the needle-suture assembly at some time during tissue penetration and at some time during retrieving. Identical parts of the assembly shown at the distinct instances during the suturing process are designated by the letters "a" and "b". The needle-suture assembly 30 is depicted after piercing the body tissue wall 42 and penetrating through the body tissue 40 until the anchoring stopper 21a is beyond the inside wall of body tissue 40. Needle 10b is depicted when retrieved from the body tissue while the suture 20 is disengaged from needle 10b and retained inside the body tissue by the anchoring stopper 21b blocking the movement out.

Figure 6:
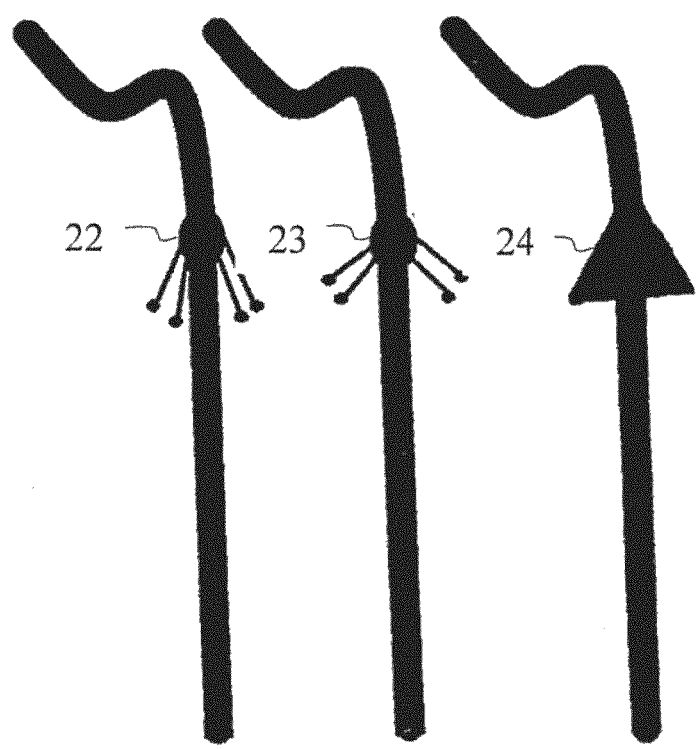

Reference is now made to FIG. 6 presenting a schematic illustration of two distinct embodiments of the anchoring stopper appended to the suture. The stopper is structured to minimize interfering with the needle-suture penetration into the body tissue yet provide the blocking action to the suture when the stopper is located beyond and near the inside wall of the body tissue when the needle is retrieving. Stopper 21 is shaped like a triangle consisting of a group of various triangular shapes. Another embodiment of the anchoring stopper is illustrated by Stopper 22 and stopper 23. In this embodiment the stopper is an umbrella like structure constructed by a plurality of rods. When the suturing assembly is penetrating the tissue, stopper 22 is shaped like a closed umbrella thus minimally interfering with the needle suture penetration into the tissue. Stopper 23 of this type is depicted when stopper getting to the internal wall of the body tissue whereas the stopper becomes shaped like an opened umbrella and thus provides the stopper blocking function.

The invention claimed is:

1. A suturing needle comprising a hollowed sharp distal portion interconnected via an open bore to a proximal portion, wherein said sharp distal portion comprises: a tip and a single notch; said notch being confined so as to be located on said open bore at said needle's distal end, opposite to said tip; said bore and said notch are adapted to accommodate a first portion of a suture; a second potion of said suture adjacent to said first portion extending along the outer surface of the needle; said suture having at least one anchoring stopper between the first and second portions; the dimensions of said anchoring stopper are greater than the dimensions of said notch, such that the entire anchoring stopper is retained by said notch outside of said open bore so as to prevent movement of the suture relative to said needle; said anchoring stopper adapted to anchor said suture within said tissue.

2. A suturing assembly comprising a suturing needle according to claim 1, and a suture; said suturing needle being configured to accommodated the end of said suture within said hollowed sharp distal portion.

3. The suturing assembly according to claim 2, wherein said hollow portion of said needle having said bore is adapted to accommodate said suture; further wherein said suture is extended from said bore via said notch after inserting said suture into said bore.

4. The suturing assembly according to claim 2, further comprising a proximal portion wherein said proximal portion of said needle is adapted for coupling with said surgical device.

5. The suturing assembly according to claim 2, wherein said suture comprises at least one said anchoring stopper.

6. The suturing assembly according to claim 5, wherein the shape of said anchoring stopper is selected from a group consisting of spherically shape, and a non limited choice of triangles or any combination thereof.

7. The suturing assembly according to claim 5, wherein said anchoring stopper comprises a plurality of rods umbrella like shaped having a main axis substantially coinciding with the longitudinal axis of said of said suture.

8. The suturing needle according to claim 1, wherein said proximal portion of said needle is adapted for coupling with surgical device.

9. The suturing needle according to claim 1, wherein said suture is extended from said bore.

10. The suturing needle according to claim 1, wherein the shape of said anchoring stopper is selected from a group consisting of spherically shape, and a non limited choice of triangles.

11. The suturing needle according to claim 1, wherein said anchoring stopper comprises a plurality of rods umbrella like shaped having a main axis substantially coinciding with the longitudinal axis of said suture.

12. A method of suturing, comprising:
   a. obtaining a suturing assembly, comprising (i) a suturing needle with a hollowed distal portion with an open bore at the distal end; and, (ii) a suture with a first portion reversibly mounted within said bore, a second portion and an anchoring stopper between the first and second portions, said second portion and the entirety of said anchoring stopper extending along the outer surface of the needle;
   b. suturing a body tissue by piercing said tissue with said distal portion of said needle, until said needle's distal portion and said anchoring stopper extend beyond said pierced tissue; and,
   c. retrograding said needle while said suture's end, which was inserted into said needle's bore, is disengaged from said suturing needle and retained by said anchoring stopper beyond said pierced tissue.

13. The method according to claim 12, wherein said suturing is provided manually.

14. The method according to claim 12, wherein said suturing is provided automatically by coupling said proximal portion of said needle with a surgical device.

15. The method according to claim 12, wherein at least a portion of said suture interconnected with said anchoring stopper remains exterior to said open bore while another portion of said suture is lying within said open bore of said suturing needle.

\* \* \* \* \*